United States Patent
Dawkins et al.

(10) Patent No.: US 11,945,761 B2
(45) Date of Patent: Apr. 2, 2024

(54) PROCESS FOR THE PRODUCTION OF CHLORINATED HYDROCARBONS

(71) Applicant: OCCIDENTAL CHEMICAL CORPORATION, Dallas, TX (US)

(72) Inventors: John L. Dawkins, Derby, KS (US); Darrell Hollis, Conway Springs, KS (US); Keith S. Kramer, Andover, KS (US); Brian Calderwood, Wichita, KS (US); Michael A. Garmon, Manvel, TX (US)

(73) Assignee: OCCIDENTAL CHEMICAL CORPORATION, Dallas, TX (US)

( * ) Notice: Subject to any disclaimer, the term of this patent is extended or adjusted under 35 U.S.C. 154(b) by 1167 days.

(21) Appl. No.: 16/320,667

(22) PCT Filed: Jul. 24, 2017

(86) PCT No.: PCT/US2017/043473
§ 371 (c)(1),
(2) Date: Jan. 25, 2019

(87) PCT Pub. No.: WO2018/022491
PCT Pub. Date: Feb. 1, 2018

(65) Prior Publication Data
US 2021/0355052 A1    Nov. 18, 2021

Related U.S. Application Data

(60) Provisional application No. 62/366,680, filed on Jul. 26, 2016.

(51) Int. Cl.
C07C 17/10    (2006.01)
B01D 3/32    (2006.01)
(Continued)

(52) U.S. Cl.
CPC .............. *C07C 17/10* (2013.01); *B01D 3/322* (2013.01); *C07C 17/25* (2013.01); *C07C 19/01* (2013.01); *C07C 2523/745* (2013.01)

(58) Field of Classification Search
CPC ...................................................... C07C 17/10
See application file for complete search history.

(56) References Cited

U.S. PATENT DOCUMENTS

| 4,650,914 A | 3/1987 | Woodard |
| 8,907,147 B2 | 12/2014 | Wang et al. |

(Continued)

FOREIGN PATENT DOCUMENTS

| JP | 2011507877 | 3/2011 |
| JP | 2016-509001 A | 3/2016 |

(Continued)

OTHER PUBLICATIONS

PowderBulkSolids ("Mixing Solutions and Slurries—Effectively, Economically, and Safely" Feb. 24, 2012). (Year: 2012).*

(Continued)

*Primary Examiner* — Medhanit W Bahta
(74) *Attorney, Agent, or Firm* — Kenner Renner; Arthur M. Reginelli

(57) ABSTRACT

A process of the type for producing 1,1,1,2,3-pentachloropropane by introducing 1,1,1,3-tetrachloropropane, chlorine, and Lewis acid catalyst, optionally in the presence of carbon tetrachloride, the improvement comprising introducing the Lewis acid as a slurry within a chlorinated hydrocarbon.

12 Claims, 2 Drawing Sheets

(51) Int. Cl.
    *C07C 17/25*     (2006.01)
    *C07C 19/01*     (2006.01)

(56) References Cited

U.S. PATENT DOCUMENTS

| | | |
|---|---|---|
| 2004/0225166 A1 | 11/2004 | Wilson et al. |
| 2009/0216055 A1 | 8/2009 | Wilson et al. |
| 2014/0206911 A1 | 7/2014 | Sherwood et al. |
| 2016/0002127 A1 | 1/2016 | Tirtowidjojo et al. |
| 2017/0081263 A1* | 3/2017 | Klausmeyer ............ C07C 17/25 |

FOREIGN PATENT DOCUMENTS

| | | | |
|---|---|---|---|
| WO | 20140134377 A2 | 9/2014 | |
| WO | WO-2015175791 A1 * | 11/2015 | ............ C07C 17/25 |

OTHER PUBLICATIONS

Kars-Jordan, F. "Agitation Handbook" 2007, pp. 1-90 (Year: 2007).*
Office Action for corresponding Japanese Patent Application No. 2019-503566 dated Mar. 29, 2021.
International Search Report and Written Opinion for corresponding PCT/US2017/043469 dated Sep. 20, 2017.
First Examination Report in India Application No. 202118023344 dated Feb. 17, 2022.

* cited by examiner

PROCESS FOR THE PRODUCTION OF CHLORINATED HYDROCARBONS

This application is a National-Stage application of PCT/US2017/043473 filed on Jul. 24, 2017, which claims the benefit of U.S. Provisional Application Ser. No. 62/366,680 filed on Jul. 26, 2016, which are incorporated herein by reference.

FIELD OF THE INVENTION

Embodiments of the present invention provide processes for the production of chlorinated hydrocarbons, particularly 1,1,1,2,3-pentachloropropane and 1,1,2,3-tetrachloropropene.

BACKGROUND OF THE INVENTION

Hydrofluoroolefins (HFOs) have been proposed as "fourth generation" refrigerants. These compounds have also been proposed for use as blowing agents, biocides, and monomer feedstock. Most industrially useful synthetic techniques require chlorinated hydrocarbon feedstocks to produce the HFOs. In particular, 2,3,3,3-tetrafluoropropene (HFO-1234yf) can be produced by employing 1,1,2,3-tetrachloropropene (HCC-1230xa) feedstock.

U.S. Publication No. 2009/0216055A1 teaches a method for producing 1,1,2,3-tetrachloropropene by dehydrochlorinating 1,1,1,2,3-pentachloropropane (HCC-240db). This patent publication teaches that 1,1,1,2,3-pentachloropropane can be produced in a single reaction vessel by heating a reaction mixture of 1,1,1,3-tetrachloropropane (HCC-240fa), chlorine, and a Lewis acid catalyst. The Lewis acid catalyst dehydrochlorinates the 1,1,1,3-tetrachloropropane to form 1,1,3-trichloropropene, and then the 1,1,3-trichloropropene reacts with chlorine in the presence of the catalyst to produce 1,1,1,2,3-pentachloropropane. The catalyst (e.g. ferric chloride) is added to the reactor either continuously or periodically and is generally maintained at 30 to 1000 ppm. The product is fed, either continuously or periodically, to a reactive distillation system where the 1,1,1,2,3-pentachloropropane is dehydrochlorinated to 1,1,2,3-tetrachloropropene in the presence of a Lewis acid catalyst such as the ferric chloride. The distillation system employed includes a reaction zone, a separation zone, and a condensing zone. The liquid in the reaction zone is heated and agitated. Heat can be provided through a jacket on the vessel, by internal heat exchangers, or by external heat exchangers, and the agitation can be provided via pump circulation or stirring.

Because 1,1,2,3-tetrachloropropene is an important feedstock for the synthesis of certain HFOs, there is a desire to improve the efficiency of the processes for the production of 1,1,2,3-tetrachloropropene.

SUMMARY OF THE INVENTION

One or more embodiments of the present invention provide a process of the type for producing 1,1,1,2,3-pentachloropropane by introducing 1,1,1,3-tetrachloropropane, chlorine, and Lewis acid catalyst, optionally in the presence of carbon tetrachloride, the improvement comprising introducing the Lewis acid as a slurry within a chlorinated hydrocarbon.

Other embodiments of the present invention provide a process of the type for converting 1,1,1,2,3-pentachloropropane to 1,1,2,3-tetrachloropropene by reactive distillation in the presence of a Lewis acid catalyst, the improvement comprising heating a crude product stream including 1,1,1,2,3-pentachloropropane and Lewis acid catalyst within a reboiler operating at conditions that inhibit the reaction or formation of deposits within the distillation column and the reboiler.

Yet other embodiments of the present invention provide a process for producing 1,1,1,2,3-pentachloropropane, the process comprising (i) providing a slurry of a Lewis acid catalyst within a chlorinated hydrocarbon; (ii) continuously circulating the slurry through a slurry loop in fluid communication with a reactor; and (iii) introducing into the reactor 1,1,1,3-tetrachloropropane, chlorine, and the slurry.

Still other embodiments of the present invention provide a process for converting 1,1,1,2,3-pentachloropropane to 1,1,2,3-tetrachloropropane, the process comprising (i) providing a mixture of 1,1,1,2,3-pentachloropropane and Lewis acid catalyst; (ii) heating the mixture within a forced recirculation reboiler; and (iii) introducing the heated mixture from the forced recirculation reboiler to a column to thereby vaporize 1,1,2,3-tetrachloropropene formed by heating the 1,1,1,2,3-pentachloropropane in the presence of Lewis acid catalyst.

DETAILED DESCRIPTION OF ILLUSTRATIVE EMBODIMENTS

Figure 1:
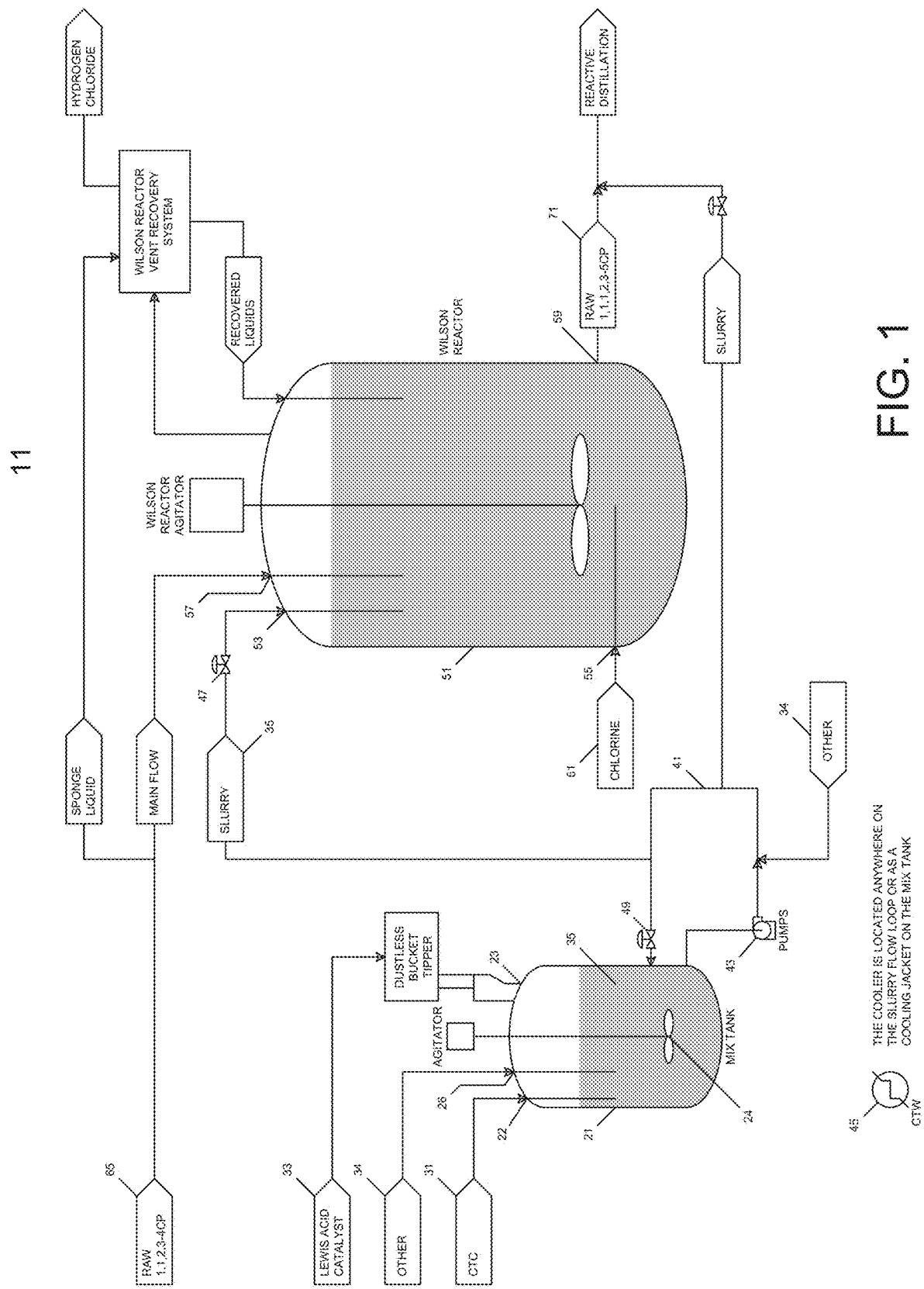
FIG. 1 is a schematic view of a system for the preparation of 1,1,1,2,3-pentachloropropane wherein the process includes a slurry loop for delivering Lewis acid to the reactor.

Embodiments of the invention are based, at least in part, on the discovery of a process for the synthesis of 1,1,1,2,3-pentachloropropane by chlorinating 1,1,1,3-tetrachloropropane, wherein one or more Lewis acid catalysts, such as ferric chloride, is delivered to a reaction vessel from a slurry system wherein the catalyst is slurried within a chlorinated hydrocarbon (e.g. carbon tetrachloride). It is believed that by separately preparing a catalyst slurry, efficiencies can be achieved and problems associated with the Lewis acid catalysts, such as handling problems and its propensity to absorb water, can be avoided. This process also will advantageously allow for more finite controls on the introduction of the catalyst to the reactor.

According to other embodiments, 1,1,1,2,3-pentachloropropane crude is dehydrochlorinated to 1,1,2,3-tetrachloropropene by reactive distillation through a distillation technique that heats the crude within a forced circulation reboiler. The flow velocity and heat flux within the reboiler are maintained to prevent fouling within the distillation system. Indeed, it has been discovered that localized hot spots within the distillation system cause catalyst residues to bake onto the surface of the system. Thus, while the prior art teaches that 1,1,1,2,3-pentachloropropane crude can be directly treated by reactive distillation to form 1,1,2,3-tetrachloropropene, it has now been contemplated that specific distillation systems can give rise to process efficiencies. Additionally, since the reactive distillation takes place in the presence of threshold levels of Lewis acid catalyst (e.g. ferric chloride), further efficiencies are contemplated by employing the same or similar slurry system employed for delivering the Lewis acid catalyst to the chlorination reactor.

1,1,1,2,3-Pentachloropropane Synthesis

According to embodiments of the present invention, 1,1,1,2,3-pentachloropropane is prepared by introducing 1,1,1,3-tetrachloropropane, chlorine, Lewis acid catalyst, and optionally carbon tetrachloride. In this respect, U.S. Publication Number 2009/0216055A1 is incorporated herein by reference. As the skilled person appreciates, the 1,1,1,3-tetrachloropropane is a liquid at reaction conditions, and therefore the chlorine and the Lewis acid catalyst are added to the 1,1,1,3-tetrachloropropane liquid, which may be included within a mixture with carbon tetrachloride. In one or more embodiments, the chlorine is added as a gas and can be added to the 1,1,1,3-tetrachloropropane liquid through, for example, a tube submerged into the liquid or via one or more gaseous dispersing elements within the liquid. As the skilled person appreciates, several Lewis acid catalysts have been employed as chlorination catalysts, and practice of embodiments of the invention are not limited to specific Lewis acid catalysts. Ferric chloride is a common chlorination catalyst and/or dehydrochlorination catalyst, and therefore specific embodiments of the invention are described with reference to ferric chloride, although the skilled person can readily extend the teachings herein to other chlorination catalysts.

According to embodiments of the present invention, the Lewis acid, such as ferric chloride, which is partially soluble in the reaction medium at reaction conditions, is introduced to the 1,1,1,3-tetrachloropropane liquid as a slurry dispersed (and partially dissolved) within a chlorinated hydrocarbon liquid, such as carbon tetrachloride. In one or more embodiments, the catalyst is maintained within a liquid dispersion through continuous agitation that may be provided by, for example, a continuous circulation loop that is in communication with the vessel that contains the 1,1,1,3-tetrachloropropane liquid.

The process of one or more embodiments of the present invention can be described with reference to FIG. 1. As shown, system 11 includes Lewis acid mix tank 21, which is in fluid communication with reactor 51 (which may be referred to as chlorination reactor 51) through a circulation loop 41. Slurry tank 21 receives chlorinated hydrocarbon (e.g. carbon tetrachloride) 31 through inlet 22 and Lewis acid catalyst 33 through inlet 23. Slurry tank 21 may also optionally receive other materials 34, such as additional solvents, catalysts, catalyst ligands, or recycle streams captured downstream in the process, through inlet 26. In one or more embodiments, carbon tetrachloride 31 may be fed continuously, or in other embodiments it may be periodically injected, into slurry tank 21 through inlet 22. Likewise, Lewis acid catalyst 33 may be periodically added to slurry tank 21, or in other embodiments, Lewis acid catalyst 33 may be continuously charged to slurry tank 21 by employing continuous feeding apparatus. For example, Lewis acid catalyst 33 can be charged to slurry tank 21 by employing a dustless bucket tipper.

A slurry 35 of carbon tetrachloride 31 and Lewis acid catalyst 33 is formed by agitating the mixture within slurry tank 21 via one or more mixing elements 24, which may include agitation devices or baffles. Mixing elements 24 may be operated in a manner to substantially disperse the Lewis acid catalyst within the chlorinated hydrocarbon liquid (e.g. carbon tetrachloride); in particular embodiments, agitation is sufficient to achieve a substantially homogeneous concentration of the Lewis acid within the chlorinated hydrocarbon.

Slurry 35 is continuously circulated through a circulation loop 41 via one or more pumps 43 that are upstream of reactor 51, which pumps may also advantageously maintain pressure within loop 41. Adequate pressure may also be maintained within loop 41 through the assistance of a back-pressure valve 49, which is downstream of where loop 41 delivers slurry 35 to reactor 51 (i.e. downstream of valve 47 within loop 41). Slurry 35 moving through loop 41 may be heated or cooled by heating or cooling elements 45. Other materials 34, such as those described above, may also optionally be injected into loop 41. In one or more embodiments, the mixing of the various constituents within slurry 35 can be enhanced by one or more in-line mixers, which are not shown. Circulation loop 41 also includes a valve 47 that, when in the open position, allows slurry 35 to feed reactor 51. When valve 47 is in its closed position, slurry 35 circulates through loop 41 back to mix tank 21. Valve 47 may include a control valve or solenoid valve that can be controlled by a signal flow sensor or similar device.

Reactor 51 receives slurry 35 from loop 41 via inlet 53. Reactor 51 also receives chlorine 61 via inlet 55 and 1,1,1,3-tetrachloropropane 65 through inlet 57. Additionally, reactor 51 may also optionally receive other material inputs 34, such as those described above. Reactor effluent 63 exits reactor 51 at outlet 59 as 1,1,1,2,3-pentachloropropane crude stream 71.

In one or more embodiments, the flow of slurry 35 into reactor 51, which flow is at least partially regulated by valve 47, can be proportional to the 1,1,1,3-tetrachloropropane 65 and chlorine 61 feed rate into reactor 51.

In one or more embodiments, loop 41 is maintained at a pressure that is greater than the pressure within reactor 51; in particular embodiments, the pressure within loop 41 is sufficient to create flow into reactor 51 (when valve 47 is open) while taking into account potential gravitational assistance. As the skilled person will appreciate, sufficient pressure can be maintained within loop 41 while valve 47 provides flow into reactor 51 by back-pressure valve 49. Valve 49 may include a control valve or solenoid valve that can be controlled by a signal flow sensor or similar device. In one or more embodiments, temperature controls (e.g. element 45) provide cooling to maintain the temperature of slurry 35 below the boiling point of the chlorinated hydrocarbon (e.g. below 77° C. for carbon tetrachloride). In particular embodiments, the loop temperature is maintained at from about 0 to about 80° C., in other embodiments from about 5 to about 60° C., and in other embodiments from about 10 to about 40° C.

In one or more embodiments, the concentration of Lewis acid (e.g. ferric chloride) 33 within slurry 35 may be represented as a percent solids (both dispersed and soluble) within the weight of liquid. In one or more embodiments, the percent solids ferric chloride within slurry 35 may be from about 1 to about 15 wt %, in other embodiments from about 2 to about 10 wt %, and in other embodiments from about 3 to about 7 wt %.

1,1,2,3-Tetrachloropropene Synthesis

According to embodiments of the present invention, 1,1,1,2,3-pentachloropropane crude stream can be directly treated by reactive distillation to form 1,1,2,3-tetrachloropropene. This procedure is generally known in the art, and therefore U.S. Publication Number 2009/0216055A1 is incorporated herein by reference in this regard. As suggested above, according to embodiments of the present invention, reactive distillation takes place by heating the crude product stream within a forced circulation reboiler.

The reactive distillation process of one or more embodiments can be described with reference to FIG. 2, which shows reactive distillation system 101 including distillation column 103 and reboiler 123. As generally known in the art, column 103 includes a bottom zone 103A, where column bottoms 106 in the form of liquid (which general includes about 3-5% solids) collect and form liquid level 106A. Column 103 also includes a packing zone 103B, where packing materials 104 (e.g. grid material) and/or trays 104 are located, as well as a draw tray 108. At the upper end thereof, column 103 includes head space 103C through which vapor passes out of column 103.

In one or more embodiments, reboiler 123, which may also be referred to as forced recirculation boiler 123, may include a single or multi-pass reboiler. In particular embodiments, as will be described herein below, a heating fluid or media travels shell side through reboiler 123. Practice of the present invention is not limited by the type of heating fluid employed and may include, for example, steam.

Distillation column 103 and reboiler 123 are in fluid communication via reboiler loop 111. 1,1,1,2,3-pentachloropropane crude 71 enters column 103, and more specifically, bottom 103A, at or near liquid level 106A, where crude 71 becomes included in column bottoms 106. Additional Lewis acid catalyst can be introduced to crude 71 through, for example, slurry 35 (which is described above). Column bottoms 106 enter loop 111 through outlet 105. The velocity of column bottoms 106 flowing through loop 111 is regulated by, for example, pump 115. In one or more embodiments, the velocity of column bottom 106 flowing through loop 111 is maintained at a rate sufficient to reduce tube wall temperatures within reboiler 123 and thereby inhibit reactions and/or the formation of deposits within reboiler 123. Column bottoms 106 enter reboiler 123 at inlet 125 and circulate tube side within reboiler 123. In one or more embodiments, the velocity of column bottoms 106 through reboiler 123 is at least 1, in other embodiments at least 3, and in other embodiments at least 5 m/s. In these or other embodiments, the velocity of column bottoms 106 through reboiler 123 is from about 1 to about 20, in other embodiments from about 2 to about 12, and in other embodiments from about 3 to about 9 m/s.

As suggested above, column bottoms 106 travel tube side through reboiler 123 where they are subjected to heat that is transferred from heating fluid 127 (e.g. steam) introduced through inlet 126 shell side of bottoms 106. In one or more embodiments, heat flux across the tubes within reboiler 123 is less than 44, in other embodiments less than 33, and in other embodiments less than 22 kW/m². In these or other embodiments, the heat flux across the tubes within reboiler 123 is from about 5 to about 44 kW/m², in other embodiments from about 7 to about 33 kW/m², and in other embodiments from about 10 to about 22 kW/m².

The heating of column bottoms 106, which includes 1,1,1,2,3-pentachloropropene and Lewis acid catalyst (e.g. ferric chloride), causes the dehydrochlorination of the 1,1,1,2,3-pentachloropropane to produce 1,1,2,3-tetrachloropropene.

Column bottoms 106 exit reboiler at exit 129, as a heated liquid, and are injected into column 103 at inlet 107, which is positioned below packing zone 103B; in particular embodiments, column bottoms 106 enter at or near liquid level 106A. Column bottoms 106 leaving reboiler 123 through outlet 129 are heated to an extent that at least certain target constituents, such as the 1,1,2,3-tetrachloropropene, will flash (i.e. boil) due to pressure differentials experienced upon entry into column 103, and at least portions thereof will travel through packing space 103B toward head space 103C and ultimately exit vapor outlet 109. Also, in one or more embodiments, reboiler 123 may be located at a lower elevation relative to the bottom of distillation column 103 to thereby provide sufficient hydrostatic pressure and thereby prevent premature boiling of the column bottoms within reboiler 123. Accordingly, the combination of fluid velocity through loop 111, heat reflux within reboiler 123, and the pressure maintained within loop 111 serve to inhibit reactions and/or the formation of deposits onto the tube walls or within distillation column 103.

In one or more embodiments, vapor (from the heating of column bottoms 106) may partially condense at packing space 103B and at least portions thereof may be removed from column 103 through draw tray 108. This condensate, which is rich in 1,1,2,3-tetrachloropropene, can be recirculated back to the process for several advantageous uses. For example, draw stream 117B, which may be referred to as seal face flush 117B, can be routed to one or more pumps, such as pump 117A, to provide a constant seal flush, which advantageously maintains constant pressure on the rotary seal face and maintains the seal in proper working order for long periods of time. Also, draw stream 117C, which may also be referred to as instrument flush 117C, can be routed to one or more instruments, such as level instrumentation within bottom zone 103A, which can provide constant flush on instrumentation and thereby inhibit solids build up on the instruments. In these or other embodiments, condensate from draw tray 108 can also be collected in tank 117, which advantageously allows for volume build up that can be subsequently used, for example, during startup of the reactor.

As the skilled person will appreciate, the desired 1,1,2,3-tetrachloropropene will exit distillation column 103 as a vapor stream 132 through vapor outlet 109 of distillation column 103. Vapor stream 132 may then be routed through condenser 136, which causes the condensation of the desired chlorinated hydrocarbon 138 (i.e. 1,1,1,2,3-pentachloropropane), which may also be referred to as condensate stream 138, while allowing lighter materials (as well as uncondensable materials) to exit as a light-end stream 140. A portion of condensate stream 138 may be routed back to column 103 via a distributor (not shown) through stream 139 and into head space 103C to reflux the packing. The remainder of condensate 138 is collected as the desired product. Depending on the desired level of purification, further distillation and purification of condensate 138 can be accomplished in downstream processing.

Figure 2:
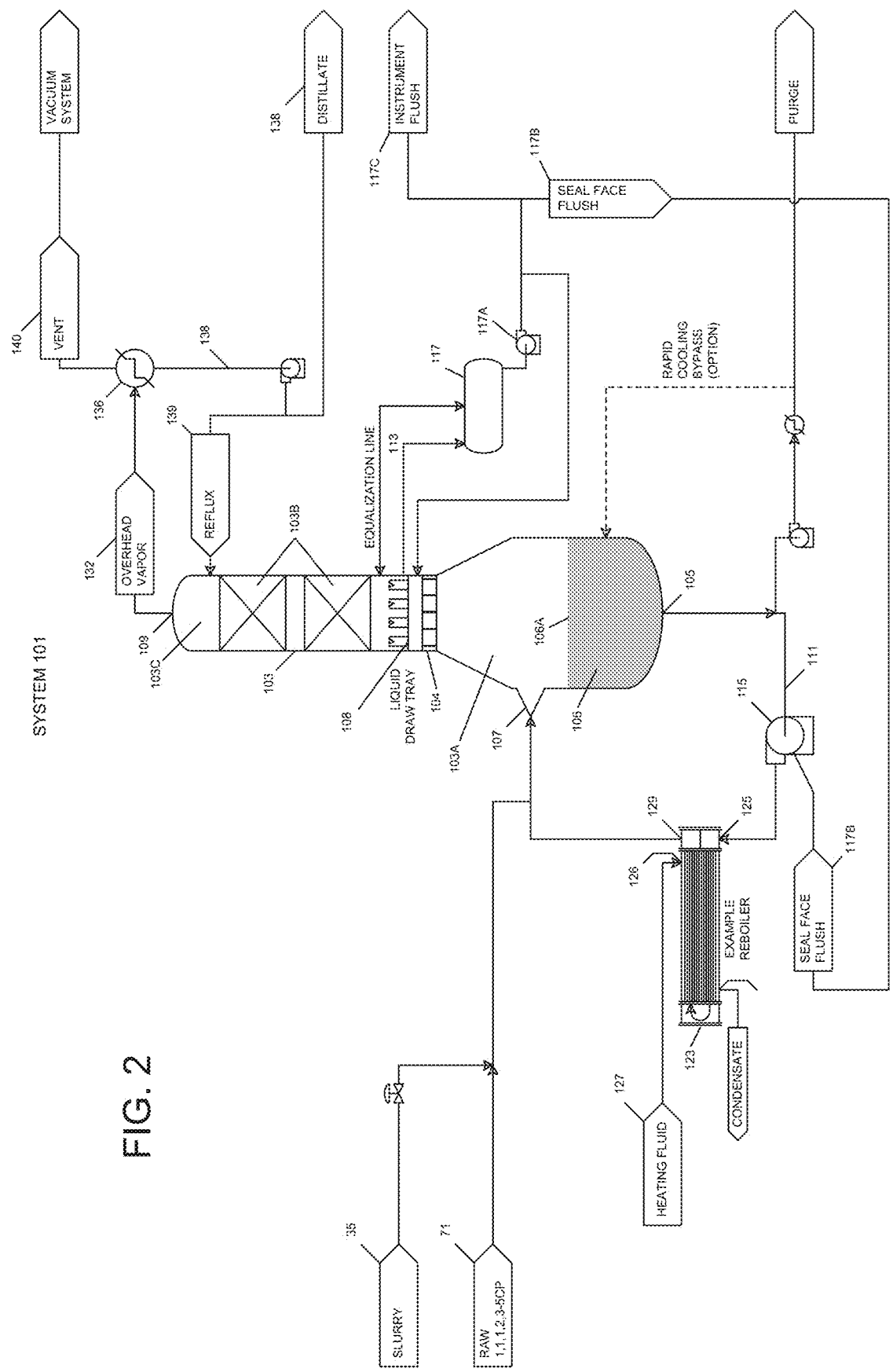
FIG. 2 is a schematic view of a system for dehydrochlorinating 1,1,1,2,3-pentachloropropane in the presence of a Lewis acid.

Additionally, as shown in both FIGS. 1 and 2, slurry 35, which includes Lewis acid from circulation loop 41, can be combined with 1,1,1,2,3-pentachloropropane crude stream 71 through valve 48 to provide sufficient Lewis acid to catalyze the dehydrochlorination reaction. As specifically shown in FIG. 2, slurry 35 can be combined with 1,1,1,2,3-pentachloropropane crude stream 71 prior to crude stream 71 entering column 103. In other embodiments, which are not shown, slurry 35 can be directly introduced to column 103 or to loop 111.

Various modifications and alterations that do not depart from the scope and spirit of this invention will become apparent to those skilled in the art. This invention is not to be duly limited to the illustrative embodiments set forth herein.

What is claimed is:

1. A process for producing 1,1,2,3-tetrachloropropene, the process comprising
providing, within a slurry system, a slurry including Lewis acid catalyst within a chlorinated hydrocarbon, where the Lewis acid catalyst is introduced to the slurry system via a dustless bucket tipper;

continuously agitating the slurry to form an agitated slurry;

introducing, to a reaction vessel, 1,1,1,3-tetrachloropropane, chlorine, and the agitated slurry, the reaction vessel optionally further including carbon tetrachloride;

allowing the 1,1,1,3-tetrachloropropane to chlorinate to the 1,1,1,2,3-pentachloropropane in the presence of the Lewis acid catalyst which is within the agitated slurry, the step of allowing the 1,1,1,3-tetrachloropropane to chlorinate thereby forming a crude 1,1,1,2,3-pentachloropropane stream; and introducing the crude 1,1,1,2,3-pentachloropropane stream to a reactive distillation column to thereby produce the 1,1,2,3-tetrachloropropene, and introducing an additional amount of the agitated slurry to the crude 1,1,1,2,3-pentachloropropane stream.

2. The process of claim 1, where the step of continuously agitating includes continuously agitating the slurry within a continuously-stirred slurry tank of the slurry system.

3. The process of claim 1, where the chlorinated hydrocarbon is carbon tetrachloride.

4. The process of claim 3, where the slurry includes from about 1 to about 15 wt % of the Lewis acid catalyst dispersed or dissolved within the carbon tetrachloride.

5. The process of claim 1, where the Lewis acid catalyst is ferric chloride.

6. The process of claim 1, where concentration of the Lewis acid catalyst within the slurry is homogenous.

7. A process for producing 1,1,1,2,3-pentachloropropane, the process comprising providing, within a slurry system, a slurry including Lewis acid catalyst within a chlorinated hydrocarbon;

continuously agitating the slurry to form an agitated slurry, where the step of continuously agitating includes continuously circulating the slurry through a slurry loop of the slurry system, where the slurry system includes a valve, where when the valve is in an open position, a step of allowing the agitated slurry to feed to a reaction vessel occurs, and where when the valve is in a closed position, a step of circulating the agitated slurry through the slurry loop and back to a mix tank occurs;

introducing, to the reaction vessel, 1,1,1,3-tetrachloropropane, chlorine, and the agitated slurry, the reaction vessel optionally further including carbon tetrachloride; and allowing the 1,1,1,3-tetrachloropropane to chlorinate to the 1,1,1,2,3-pentachloropropane in the presence of the Lewis acid catalyst which is within the agitated slurry.

8. The process of claim 7, where the 1,1,1,3-tetrachloropropane, chlorine, and Lewis acid catalyst are introduced within a reactor, and where the slurry loop is maintained at a pressure in excess of a pressure within the reactor.

9. The process of claim 8, where a temperature of the slurry within the slurry loop is maintained at a temperature below the boiling point of carbon tetrachloride.

10. A process for producing 1,1,1,2,3-pentachloropropane, the process comprising:
  (i) providing, within a slurry system, a slurry of a Lewis acid catalyst within a chlorinated hydrocarbon;
  (ii) continuously circulating the slurry through a slurry loop in fluid communication with a reactor, to thereby form an agitated slurry, where the slurry loop includes a back-pressure valve for maintaining adequate pressure within the slurry loop, where the back-pressure valve is downstream of where the slurry loop provides the agitated slurry to the reactor;
  (iii) introducing into the reactor 1,1,1,3-tetrachloropropane, chlorine, and the agitated slurry; and
  (iv) allowing the 1,1,1,3-tetrachloropropane to chlorinate to the 1,1,1,2,3-pentachloropropane in the presence of the Lewis acid catalyst which is within the agitated slurry.

11. The process of claim 10, where the chlorinated hydrocarbon is carbon tetrachloride.

12. The process of claim 10, where the Lewis acid catalyst is ferric chloride.

\* \* \* \* \*